(12) United States Patent
Wu et al.

(10) Patent No.: US 9,644,008 B2
(45) Date of Patent: May 9, 2017

(54) DEGLYCOSYLATED HEMAGGLUTININ AND MANUFACTURE THEREOF (71) Applicant: National Tsing Hua University, Hsinchu (TW)

(72) Inventors: Suh-Chin Wu, Hsinchu (TW); Wen-Chun Liu, Hsinchu (TW); Yun-Ju Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 72 days.

(21) Appl. No.: 14/201,276

(22) Filed: Mar. 7, 2014

(65) Prior Publication Data

US 2015/0183833 A1 Jul. 2, 2015

(30) Foreign Application Priority Data

Dec. 27, 2013 (TW) .............................. 102148653 A (51) Int. Cl.
*C07K 14/005* (2006.01)
*A61K 39/12* (2006.01)
*C12N 7/00* (2006.01)

(52) U.S. Cl.
CPC ............ *C07K 14/005* (2013.01); *A61K 39/12* (2013.01); *C12N 7/00* (2013.01); *C12N 2760/16034* (2013.01); *C12N 2760/16122* (2013.01); *C12N 2760/16134* (2013.01); *C12N 2760/16151* (2013.01)

(58) Field of Classification Search
None
See application file for complete search history.

(56) References Cited

PUBLICATIONS

Roberts et al. Role of conserved glycosylation sites in maturation and transport of influenza A virus hemagglutinin. J Virol. Jun. 1993;67(6):3048-60.*
GenBank: AAW72226.1. HA [Influenza A virus (A/duck/Shandong/093/2004(H5N1))]. Dated Feb. 6, 2005.*
GenBank: ABW90134.1. hemagglutinin [Influenza A virus (A/Viet Nam/1203/2004(H5N1))]. Dated Nov. 14, 2007.*
Esposito et al. Live attenuated intranasal influenza vaccine. Hum Vaccin Immunother. Jan. 2012;8(1):76-80. Epub Jan. 1, 2012.*
Imperiali et al. Effect of N-linked glycosylation on glycopeptide and glycoprotein structure. Current Opinion in Chemical Biology 1999, 3:643-649.*
Tate et al. Glycosylation of the hemagglutinin modulates the sensitivity of H3N2 influenza viruses to innate proteins in airway secretions and virulence in mice. Virology. Apr. 25, 2011;413(1):84-92. Epub Feb. 24, 2011.*
Dormitzer et al. New technologies for influenza vaccines. Hum Vaccin Immunother. Jan. 2012;8(1):45-58. Epub Jan. 1, 2012.*
Aguilar-Yanez et al. An influenza A/H1N1/2009 hemagglutinin vaccine produced in *Escherichia coli*. PLoS One. Jul. 22, 2010;5(7):e11694.*
Wagner et al. N-Glycans attached to the stem domain of haemagglutinin efficiently regulate influenza A virus replication. Journal of General Virology (2002), 83, 601-609.*

* cited by examiner

*Primary Examiner* — Nick Zou
(74) *Attorney, Agent, or Firm* — Muncy, Geissler, Olds & Lowe, P.C.

(57) ABSTRACT

The invention provides a deglycosylated hemagglutinin, wherein the glycosylation site(s) on the stem region is removed. The deglycosylated hemagglutinin may induce neutralizing antibody against influenza virus, and cross-reactive protection against different virus. The invention also provides a method for manufacturing deglycosylated hemagglutinin, comprising aligning two or more hemagglutinin stem sequences of influenza virus, identifying the high conserved N-glycosylation site, and removing the high conserved N-glycosylation site. Thus, the N-glycosylation site cannot be glycosylated.

3 Claims, 7 Drawing Sheets

H5HA(A/Thailand/KAN-1/2004)    pH1HA(A/Texas/05/2009)

Stem region

Asn23
Asn11
Asn10
Asn484

Asn45
Asn33
Asn32
Asn503

SEQUENCE LISTING

```
<160> NUMBER OF SEQ ID NOS: 2

<210> SEQ ID NO 1
<211> LENGTH: 576
<212> TYPE: PRT
<213> ORGANISM: Influenza A virus
<220> FEATURE:
<223> OTHER INFORMATION: H5N1 H5HA (A/Thailand/KAN-1/2004)

<400> SEQUENCE: 1

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140
```

```
Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ser
        515                 520                 525

Gly Arg Leu Val Pro Arg Gly Ser Pro Met Lys Gln Ile Glu Asp Lys
    530                 535                 540

Ile Glu Glu Ile Leu Ser Lys Ile Tyr His Ile Glu Asn Glu Ile Ala
545                 550                 555                 560

Arg Ile Lys Lys Leu Ile Gly Glu Val Gly His His His His His His
```

```
                            565                 570                 575

<210> SEQ ID NO 2
<211> LENGTH: 582
<212> TYPE: PRT
<213> ORGANISM: Influenza A virus
<220> FEATURE:
<223> OTHER INFORMATION: pH1N1 H1HA (A/Texas/05/2009)

<400> SEQUENCE: 2

Met Lys Phe Leu Val Asn Val Ala Leu Val Phe Met Val Val Tyr Ile
1               5                   10                  15

Ser Tyr Ile Tyr Ala Ala Asp Thr Leu Cys Ile Gly Tyr His Ala Asn
            20                  25                  30

Asn Ser Thr Asp Thr Val Asp Thr Val Leu Glu Lys Asn Val Thr Val
        35                  40                  45

Thr His Ser Val Asn Leu Leu Glu Asp Lys His Asn Gly Lys Leu Cys
    50                  55                  60

Lys Leu Arg Gly Val Ala Pro Leu His Leu Gly Lys Cys Asn Ile Ala
65                  70                  75                  80

Gly Trp Ile Leu Gly Asn Pro Glu Cys Glu Ser Leu Ser Thr Ala Ser
                85                  90                  95

Ser Trp Ser Tyr Ile Val Glu Thr Ser Ser Ser Asp Asn Gly Thr Cys
            100                 105                 110

Tyr Pro Gly Asp Phe Ile Asp Tyr Glu Glu Leu Arg Glu Gln Leu Ser
        115                 120                 125

Ser Val Ser Ser Phe Glu Arg Phe Glu Ile Phe Pro Lys Thr Ser Ser
    130                 135                 140

Trp Pro Asn His Asp Ser Asn Lys Gly Val Thr Ala Ala Cys Pro His
145                 150                 155                 160

Ala Gly Ala Lys Ser Phe Tyr Lys Asn Leu Ile Trp Leu Val Lys Lys
                165                 170                 175

Gly Asn Ser Tyr Pro Lys Leu Ser Lys Ser Tyr Ile Asn Asp Lys Gly
            180                 185                 190

Lys Glu Val Leu Val Leu Trp Gly Ile His His Pro Ser Thr Ser Ala
        195                 200                 205

Asp Gln Gln Ser Leu Tyr Gln Asn Ala Asp Ala Tyr Val Phe Val Gly
    210                 215                 220

Ser Ser Arg Tyr Ser Lys Lys Phe Lys Pro Glu Ile Ala Ile Arg Pro
225                 230                 235                 240

Lys Val Arg Asp Arg Glu Gly Arg Met Asn Tyr Tyr Trp Thr Leu Val
                245                 250                 255

Glu Pro Gly Asp Lys Ile Thr Phe Glu Ala Thr Gly Asn Leu Val Val
            260                 265                 270

Pro Arg Tyr Ala Phe Ala Met Glu Arg Asn Ala Gly Ser Gly Ile Ile
        275                 280                 285

Ile Ser Asp Thr Pro Val His Asp Cys Asn Thr Thr Cys Gln Thr Pro
    290                 295                 300

Lys Gly Ala Ile Asn Thr Ser Leu Pro Phe Gln Asn Ile His Pro Ile
305                 310                 315                 320

Thr Ile Gly Lys Cys Pro Lys Tyr Val Lys Ser Thr Lys Leu Arg Leu
                325                 330                 335

Ala Thr Gly Leu Arg Asn Val Pro Ser Ile Gln Ser Arg Gly Leu Phe
            340                 345                 350

Gly Ala Ile Ala Gly Phe Ile Glu Gly Gly Trp Thr Gly Met Val Asp
```

-continued

```
                355                 360                 365
Gly Trp Tyr Gly Tyr His His Gln Asn Glu Gln Gly Ser Gly Tyr Ala
        370                 375                 380

Ala Asp Leu Lys Ser Thr Gln Asn Ala Ile Asp Glu Ile Thr Asn Lys
385                 390                 395                 400

Val Asn Ser Val Ile Glu Lys Met Asn Thr Gln Phe Thr Ala Val Gly
                405                 410                 415

Lys Glu Phe Asn His Leu Glu Lys Arg Ile Glu Asn Leu Asn Lys Lys
            420                 425                 430

Val Asp Asp Gly Phe Leu Asp Ile Trp Thr Tyr Asn Ala Glu Leu Leu
            435                 440                 445

Val Leu Leu Glu Asn Glu Arg Thr Leu Asp Tyr His Asp Ser Asn Val
        450                 455                 460

Lys Asn Leu Tyr Glu Lys Val Arg Ser Gln Leu Lys Asn Asn Ala Lys
465                 470                 475                 480

Glu Ile Gly Asn Gly Cys Phe Glu Phe Tyr His Lys Cys Asp Asn Thr
            485                 490                 495

Cys Met Glu Ser Val Lys Asn Gly Thr Tyr Asp Tyr Pro Lys Tyr Ser
            500                 505                 510

Glu Glu Ala Lys Leu Asn Arg Glu Glu Ile Asp Gly Val Lys Leu Glu
        515                 520                 525

Ser Thr Arg Ile Tyr Ser Gly Arg Leu Val Pro Arg Gly Ser Pro Met
        530                 535                 540

Lys Gln Ile Glu Asp Lys Ile Glu Glu Ile Leu Ser Lys Ile Tyr His
545                 550                 555                 560

Ile Glu Asn Glu Ile Ala Arg Ile Lys Lys Leu Ile Gly Glu Val Gly
                565                 570                 575

His His His His His His
            580
```

DEGLYCOSYLATED HEMAGGLUTININ AND MANUFACTURE THEREOF

CROSS-REFERENCE TO RELATED APPLICATIONS

This Non-provisional application claims priority under 35 U.S.C. §119(a) on Patent Application No(s). 102148653 filed in Taiwan, Republic of China Dec. 27, 2013, the entire contents of which are hereby incorporated by reference.

BACKGROUND OF THE INVENTION

Field of the Invention

The present invention relates to a hemagglutinin of influenza virus, and in particular relates to a hemagglutinin of influenza virus capable of inducing the production of specific neutralizing antibodies and providing cross-protection against viruses.

Description of the Related Art

Influenza is a recurrent worldwide disease that causes annual seasonal epidemics and pandemics. The virus has an extremely wide host range, from birds to various mammalian species including humans, poultry, swine, and horses (Kalthoff et al., 2010). Influenza viruses belong to RNA virus Orthomyxoviridae family and can be classified into type A, B, and C. The genome of influenza A virus contains eight negative stranded RNA segments that encode 11 viral proteins, including three surface proteins, hemagglutinin (HA), neuraminidase (NA), and matrix protein (M2). Other encoded proteins include RNA polymerase subunits (PB1, PB2, PA), nucleoprotein (NP), nonstructural proteins (NS1, NS2) and a newly discovered pro-apoptotic PB1-F2 protein (Viswanathan et al., 2010).

Highly pathogenic avian influenza (HPAI) virus cause hundreds of millions of birds have died and severe mortality within susceptible poultry species. A novel H1N1 swine origin influenza virus emerged to cause human influenza outbreaks in 2009. Since the hemagglutinin (HA) has a high variability during influenza virus evolution, development of multivalent vaccine of influenza virus is still a challenge.

Even if in one strain of single species virus, a high percentage of a variant is still found due to virus has very high genetic variability. The current influenza vaccine almost only provides protection against the homosubtypic influenza virus.

Based on HA structure, it can also be discussed in two components, globular head and stem region. However, the multivalent vaccine is still developed by modifying the globular head region of hemagglutinin, and this method has disadvantages including (1) High-conserved glycosylation sites are not observed in globular head region so that the vaccine does not have broad-spectrum protective effects; (2) Thus, the glycan on the globular head region is generally digested by restriction enzymes to improve the effect of multivalent vaccines. If the carbon chain of the glycan is shorter, the effect of multivalent vaccines is better. However, how many carbon chain of the glycosyl group can be digested is a challenge.

BRIEF SUMMARY OF INVENTION

Since influenza virus has a high variability, it remains challenge to develop broader and more effective universal vaccines. The glycosylation site on HA of the globular head region are studied and published. However, the variability of the glycosylation site on the head region is so high that the high conserved region is difficult to be determined.

Accordingly, the invention provides a deglycosylated hemagglutinin, which can induce the cross-protective and neutralizing antibody against influenza virus, to solve the problems of the traditional multivalent vaccines.

The invention provides a HA1 module and a HA2 module, and the HA1 and HA2 are classified into a stem region and a head region, wherein glycosylation sites of the HA1 and HA2 on the stem region are removed.

In one embodiment, the hemagglutinin is a hemagglutinin of influenza virus.

In one embodiment, the deglycosylation site amino acid residue is Asn.

In one embodiment, the influenza virus comprises avian H5N1 influenza virus and novel pH1N1 influenza virus.

In one embodiment, the stem region of the avian H5N1 influenza virus comprises amino acids at positions 1 to 57 of the HA1 module and amino acids at positions 343 to 527 of the HA2 module.

In one embodiment, the deglycosylation site comprises amino acids at positions 10, 11, and 23 of the HA1 module and/or an amino acid at position 484 of the HA2 module on the stem region of the avian H5N1 influenza virus.

In one embodiment, the stem region of the novel pH1N1 influenza virus comprises amino acids at positions 1 to 63 of the HA1 module and amino acids at positions 350 to 553 of the HA2 module.

In one embodiment, the deglycosylation site comprises amino acids at position 32, 33 and 45 of the HA1 module and/or an amino acid at position 503 of the HA2 module on the stem region of the novel influenza pH1N1 virus.

The invention also provides a method for manufacturing a deglycosylated hemagglutinin, comprising: providing a hemagglutinin sequence of an influenza virus; a definition step of classifying the hemagglutinin sequences of the influenza virus into a head region and a stem region according to the structure; a determination step of determining a deglycosylation site on the stem region; a deglycosylation step of removing the N-linked glycosylations by a removal method, wherein the removal method comprises a amino acid substitution, replacement, or modification at the N-linked glycosylation sites, wherein the N-linked deglycosylated hemagglutinin of the stem region has features of influenza virus of multiple subtypes.

In one embodiment, the hemagglutinin sequence of the influenza virus comprises the sequences of avian H5N1 influenza virus and novel pH1N1 influenza virus.

In one embodiment, the glycosylation site of the HA1 module on the stem region comprises amino acids at positions 10, 11, and 23 of the avian H5N1 influenza virus and/or the glycosylation site of the HA2 module on the stem region comprises an amino acid at position 484 of the avian H5N1 influenza virus in the determination step In one embodiment, the glycosylation site of the HA1 module on the stem region comprises amino acids at positions 32, 33, and 45 of the novel pH1N1 influenza virus and/or the glycosylation site of the HA2 module on the stem region comprises an amino acid at position 503 of the novel pH1N1 influenza virus in the determination step The invention further provides a multivalent influenza virus vaccine, comprising the deglycosylated hemagglutinin of the claim 1, and a pharmaceutically acceptable adjuvant or carrier.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a deglycosylated hemagglutinin (HA), wherein the glycosylation site on the stem region of the hemagglutinin is removed.

The term "hemagglutinin (HA)" of the invention refers a homotrimeric type I transmembrane glycoprotein and the major envelope protein of influenza virus to allow the virion enters into the host cell (Skehel and Wiley, 2000). The uncleaved precursor of HA is HA0, trimerizing in endoplasmic reticulum and transferring through the Golgi apparatus to the cell surface. HA0 can be cleaved into HA1 and HA2 subunits, and the cleavage is essential for activation of membrane fusion and infectivity (Garten and Klenk, 1999; Skehel and Wiley, 2000). Based on HA structure, it can also be discussed in two components, globular head and stem region.

During antigenic variation, many amino acid sequence changes and proteins glycosylation occur. N-linked glycans on the HA of influenza A virus attach through N-glycosidic linkages to aparagine (Asn) residues of the conserved glycosylation motif Asn-X-Ser/Thr, where X may represent any amino acid except proline (Kornfeld and Kornfeld, 1985).

The location and number of glycans on the globular head of HA differ markedly between influenza strains (Abe et al., 2004; Wagner et al., 2000). Therefore, the multivalent vaccine using globular head of HA does not have a significant protection against heterosubtypic influenza viruses.

Accordingly, the invention provides a stem-deglycosylated hemagglutinin, and the experiments of the invention show that the stem-deglycosylated hemagglutinin provide cross-reactive protection.

It should be noted that at least one glycosylation site on the stem of the HA is removed to obtain the deglycosylated HA of the invention.

The glycosylation site may be understood in the broadest sense as an amino acid moiety to which one or more saccharides may be conjugated with.

In the invention, the number of removing the glycosylation site is not limited, preferably, one or more, such as, 2, 3, 4, 5, or more glycosylation site(s) is(are) removed.

The method for removing glycosylation site is not limited. Any method for removing glycosylation site can be used. The methods include, but are not limited to, deletion, mutation, substitution, or modification of amino acids so as the amino acids cannot link glycans. One skilled in the art would select an appropriate method to achieve the deglycosylation of the invention. The "deglycosylation" of the invention means that the removal of one or more attached oligosaccharides from an amino acid, and the glycans cannot be linked to the amino acid.

In the invention, the well-conserved N-linked glycosylation site on the stem region is removed, preferably.

In one embodiment, the amino acid at positions 10, 11, 23 and/or 484 of avian H5N1 influenza virus are selected to be removed from the stem region. For example, the amino acids at positions 10, 11, and 23 of avian H5N1 influenza virus are selected, or the amino acid at position 484 of avian H5N1 influenza virus is selected.

Figure 1:
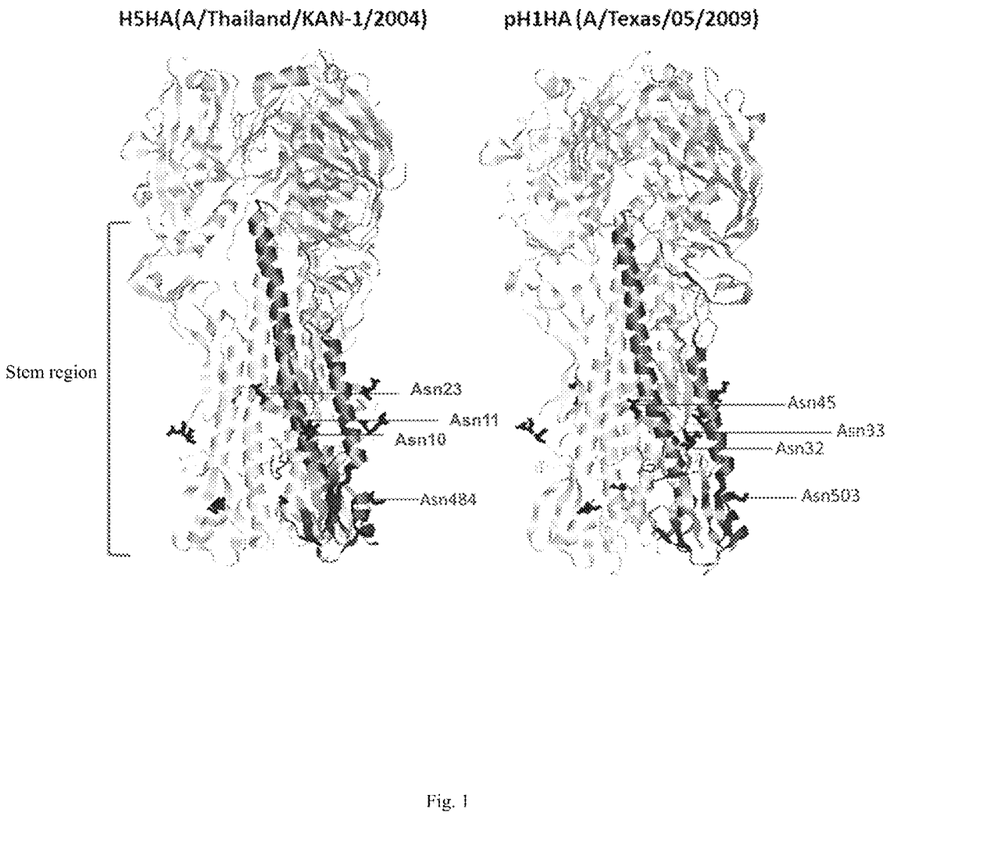
FIG. 1 illustrates the stem region and N-linked glycans of influenza virus.

In another embodiment, the amino acid at positions 32, 33, 45 and/or 503 of novel pH1N1 influenza virus are selected to be removed from the stem region HA. For example, the amino acids at positions 32, 33, and 45 of novel pH1N1 influenza virus are selected, or the amino acid at position 503 of novel pH1N1 influenza virus is selected. FIG. 1 shows the HA stem region of pH1N1 and H5N1 virus and the selected-glycosylation site in the Examples of the invention.

In a preferred embodiment, the amino acid at position 503 of novel pH1N1 influenza virus is selected to be removed from the stem region of HA.

The deglycosyalted HA of the invention can not only elicit the neutralization antibodies against influenza virus in human or animal, but also provides a cross-reaction against different influenza viruses. Therefore, the deglycosylated HA of the invention provides broad protection against various influenza viruses. Additionally, in the challenge experiment, the deglycosylated HA can effectively protect the animal against the infection of the viruses from same strain.

The invention further provides a method for manufacturing a deglycosylated HA, comprising: (1) providing a hemagglutinin sequence of an influenza virus; (2) a definition step of classifying a head region and a stem region of hemagglutinin sequences of the influenza virus depended on structure; (3) a determination step of determining a deglycosylation site of the stem region; and (4) a deglycosylation step of removing the deglycosylation site by a removal method, wherein the removal method comprises substitution, replacement, or modification of amino acid residues at the deglycosylation site, wherein the deglycosylated hemagglutinin of the stem region has various features of the different subtypes of influenza viruses.

In the invention, the definition step and determination step of the HA sequence, preferably, the HA stem region sequence, are most important to find the well-conserved glycosylation sites on the stem region.

The number of the high-conserved glycosylation site is not limited. The number of the well-conserved glycosylation site is least one, preferably, 2, 3, 4, 5, or more.

Subsequently, the genetic engineering technology is used to remove the well-conserved glycosylation site on the stem region to obtain a deglycosylatied HA. The removal method is not limited. Any well-known method can be used to remove the glycosylation site on the stem region.

The invention also provides an influenza vaccine, comprising the deglycosylated HA, and a pharmaceutically acceptable adjuvant or carrier.

The influenza vaccine comprises antigen and adjuvant. The antigen is the deglycosylated HA of the invention, which can be expressed by mammalian cells, insect cells, lower eukaryotes, or prokaryotes. Examples of mammalian cells include monkey COS cells, CHO cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Examples of insect cells consist of Sf9, Sf21 or Hi-5 cell lines. Examples of lower eukaryotes such as yeast include *Saccharomyces cerevisiae, Schizosaccharomyces pombe, Kluyveromyces strains, Candida*, or any yeast strain capable of expressing heterologous proteins. Examples of prokaryotes include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein.

As mentioned above, since the deglycosyalted HA of the invention not only can elicit the neutralization antibody against influenza virus in human or animal, but also provides a cross-reaction with different influenza viruses, the deglycosyated HA of the invention provides a broad protection against various influenza viruses.

EXAMPLE

Example 1: Preparation of Deglycosylated HA a. Construction Design

Figure 2:
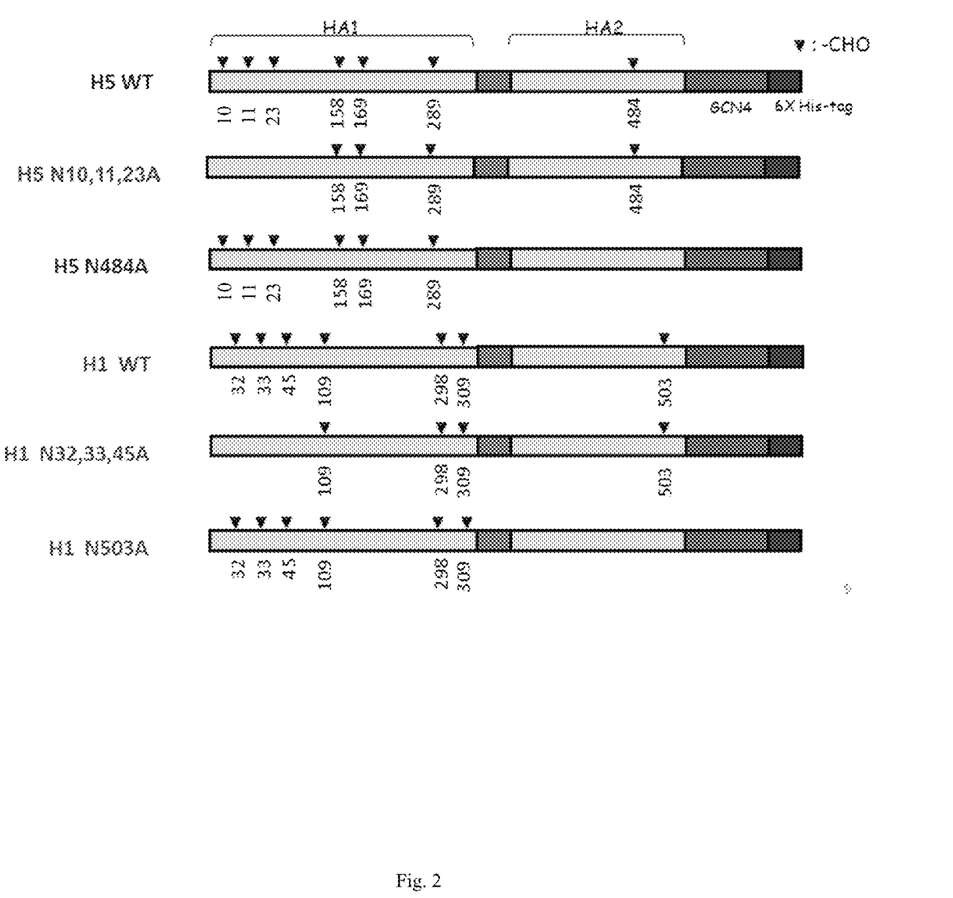
FIG. 2 illustrates the design of recombinant stem-deglycosylated HA glycoprotein.

The potential N-linked glycans were predicted by NetNGlyc Server. Site-directed mutagenesis was performed to sequentially remove N-linked glycans from the H5N1 (A/Thailand/KAN-1/2004) HA and 2009 pandemic H1N1 (A/Texas/05/2009) HA. Removal of N-glycosylation sites was achieved by substituting asparagine (Asn, N) with alanine (Ala, A) to abrogate glycosylation sequence motif Asn-X-Ser/Thr (i.e., H5N1(KAN-1) HA Asn10,11,23 [NNSTEQVDTIMEKNVT→AASTEQVDTIMEKAVT], H5N1(KAN-1) HA Asn484 [NGT→AGT] pH1N1 (Texas) HA Asn32,33,45 [NNSTDTVDTVLEKNVT→AASTDTVDTVLEKAVT], pH1N1 (Texas) HA Asn503 [NGT→AGT]). The constructs were abbreviated as "H5 N10,11,23A", "H5 N484A", "H1 N32,33,45A", and "H1 N503A", respectively as shown in FIG. 2.

b. Plasmid Preparation

The PCR product was cleaned and eluted by 35 µl ddH$_2$O and then mixed with 4 µl 10× restriction enzyme buffer and 1 µl of DpnI restriction enzyme to digest in 37° C. for 1.5 hours. The digested product was added into 100 µl TOP10 competent cell (*E. coli*). Then the sample was placed on ice for 30 mins and heat-shock at 42° C. for 30 seconds then put on ice for 2 mins immediately. The bacteria were then added to LB broth and spread onto plate (contain 0.1% ampicillin). Colonies were picked and plasmids were isolated by High-Speed Plasmid Kit (Geneaid).

c. Generation of Recombinant Bacmid

Once mutant pFastBac constructs were generated, 1 µl of transformed purified plasmid DNA was added into 100 µl of *E. coli* strain DH10Bac competent cell for transposition into the bacmid. The sample was put on ice for 35 mins and heat-shock at 42° C. for 45 seconds. Then, transformed *E. coli* was added into 1 ml of LB broth and incubated at 37° C. for 4 hrs. Finally, took 30 µl plasmid to spread on plate (concluded 0.1% Kanamycin, Gentamycin, Tetracycline, X-gal and IPTG) and incubated at 37° C. After 2 days, the white colonies, containing the recombinant bacmid, were selected.

d. Transfection

The transfection was implemented by Turbofect™ in vitro transfection reagent (Thermo). 1×10$^6$ cells/well was seeding in 6-well plate 1 hr before the experiment. 3-5 µg bacmid DNA was mixed with 8 µl Turbofect reagent and 92 µl OPTI-MEM (Gibco), then placed in room temperature for 15 mins. Then the sample was inoculated into the well and carried out transfection for 4.5-6 hrs. Afterward, supernatant was removed and 2 ml of SF900II SFM (Gibco) medium was added with 5% FBS.

e. Production and Purification of Recombinant HA Proteins

The first and second passage baculovirus containing recombinant bacmid DNA was prepared. 15 ml of second passage baculovirus was added into 600-1,200 ml Sf9 cells and incubated at 28° C. for 48 hours. Cells and medium were harvested and centrifuged with 2,000 rpm, 30 mins, and then the supernatant was collected.

The supernatant containing soluble form of recombinant HA proteins were concentrated into 35 ml with Amicon Millipore instrument. Then the pH value was adjusted to 7.4 and centrifuged with 10,000 rpm for 10 mins. Supernatants were harvested and bound with Ni-NTA (containing buffer A) 6 hrs or overnight in 4° C. Afterward, the resin containing recombinant HA proteins was packed and ran the ATKA Prime. The samples were eluted through buffer B (5% Glycerol, 30 mM Tris-HCL, 50 mM NaCl and 500 mM imidazole). Finally, the fractions with HA protein were collected and concentrated into 1 ml or so. The purified HA proteins were performed dialysis with PBS and stored at 4° C. or −20° C.

Example 2: Analysis of Deglycosylated HA a. SDS-PAGE

Tris-glycine SDS-polyacrylamide Gel Electrophoresis (SDS-PAGE) was used to analyze proteins expression. 5% stacking gel (H$_2$O 3.4 ml with 30% acrylamide mix 830 µl, 1M Tris (pH 6.8) 630 µl, 10% SDS 50 µl, 10% ammonium persulfate 50 µl and TEMED 5 µl) was loaded on upper layer. 12% separating gel (H$_2$O 3.3 ml with 30% acrylamide mix 4 ml, 1M Tris (pH 8.8) 2.5 ml, 10% SDS 100 µl, 10% ammonium persulfate 100 µl and TEMED 10 µl). The sample was run at 150V about 2 hours. After electrophoresis running, the SDS-PAGE gel was stained with 0.25% Coomassie Briliant Blue R-250 (Sigma) for overnight. Then, to de-stain the gel, destained buffer (300 ml methanol, 100 ml acetic acid and 600 ml ddH$_2$O) was used. According to FIG. 3A, The molecular weight of purified H5 WT was about 72 kD, and the molecular weight of "H5 N10,11,23A" and "H5 N484A" was slightly lower than 72 kD. According to FIG. 3B, H1 WT contained three major bands, indicating that some HA0 precursors were cleaved into HA1 and HA2. H1 N503A was also cleaved partially and showed the pattern similar to H1 WT. Especially, compared to H1WT, the lower size of HA2 confirmed the H1 N503A glycan elimination. However, H1 N32,33,45A only showed unique major band, with molecular size slightly smaller than 72 kDa.

b. Western Blotting

Figure 3:
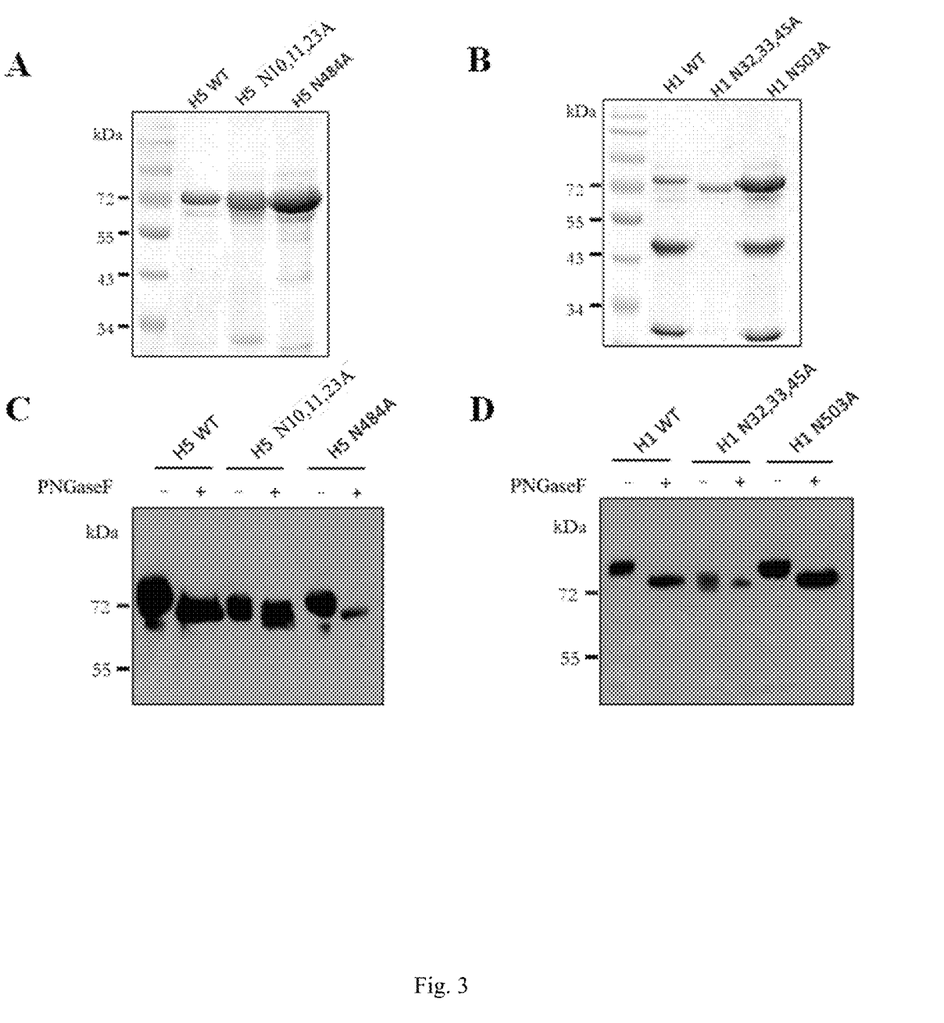
FIG. 3A-3D illustrate the difference between the molecule weight of wild-type HA and stem-deglycosylated HA.

1~2 μg proteins were mixed with 5 μl of loading dye containing DTT and heated in boiling water for 5 mins. The solutions were loaded in SDS-PAGE gel. HA proteins were mixed with denaturing buffer in 9:1 ratio and boiled for 10 min. Then the samples were treated by PNGaseF 1.5 μl and mixed with G7 buffer 2 μl, 10% NP-40 2 μl in 37° C. for 2 hr. Tris-glycine SDS-polyacrylamide Gel Electrophoresis (SDS-PAGE) was used to analyze proteins expression. The sample was run at 150V about 2 hours. After electrophoresis, the gel was transferred onto nitro-cellulose (NC) paper by electricity 135V, 35 mins. 5% milk was used to block NC paper for 2 hrs or overnight. Afterward, anti-His conjugated HRP antibody (GeneTex) was added in 1:5,000 dilutions with TBST buffer and recognized for 1 hr to carry out. At last, substrate was used as detection reagents. To confirm the characterization of WT and stem-deglycosylated glycoproteins, PNGase F was used to cleave all N-linked glycans. After PNGaseF treatment, the molecular weights of H5 N10,11,23A and H5 N484A were decreased to the same size as H5 WT (FIG. 3C). Likewise, the molecular weights of H1 N32,33,45A and H1 N503A shifted to the same size as H1 WT after PNGaseF treatment (FIG. 3D).

3. Immunization Assay of Deglycosylated HA a. Mouse Immunization 6 to 8 weeks BALB/c mice were purchased from National Laboratory Animal Center. Five mice in each group were immunized twice via intramuscular injection with 20 μg recombinant proteins (rH5HA WT, rH5HA N10,11,23A, rH5HA N484A, rH1HA WT, rH1HA N32, 33, 45A, rH1HA N503A) and 10 μg CpG/10% PELC. Blood samples were collected at 14 days after second dose of immunization. Serum sample were inactivated at 56° C. for 30 mins and stored at −20° C. for the following assays.

b. Titer of HA Specific IgG

Figure 4:
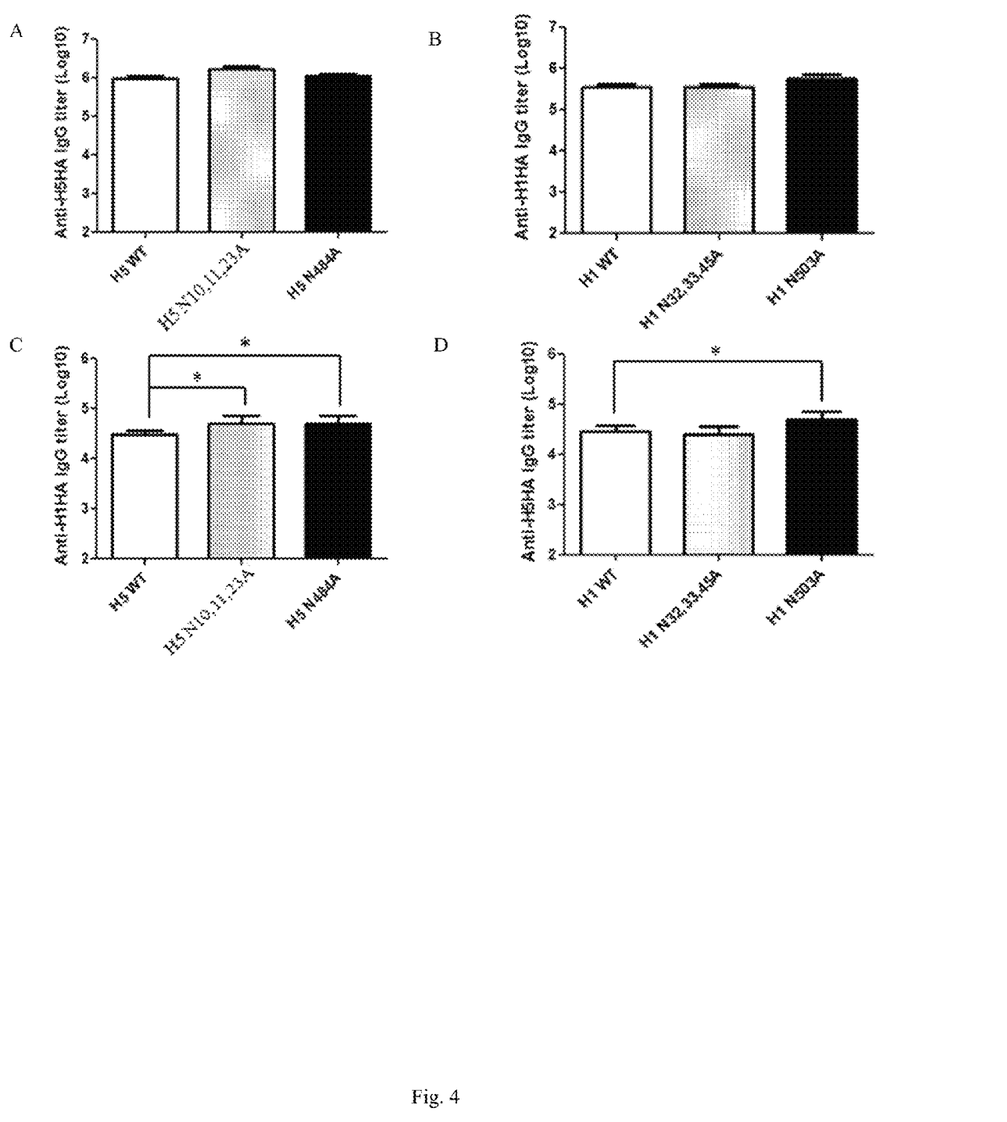
FIG. 4A-4D illustrate the titer of anti-H5N1 and anti-pH1N1 antibody elicited by wild-type HA and deglycosylated HA.

2 μg/ml of purified rH5HA WT, rH5HA N10,11,23A, rH5HA N484A, rH1HA WT, rH1HA N32, 33, 45A or rH1HA N503A proteins were coated on 96 well plates overnight and then blocked with ELISA blocking buffer (PBS and 1% BSA) for 1 hr followed by serial dilutions of each sample for 1 hour, and were subsequently washed by PBST (PBS and 0.05% Tween-20). Following, samples were incubated for 1 hour with anti-mouse IgG conjugated HRP (1:30,000) (GeneTex). Then, plates were further washed by PBST twice. Finally, samples were incubated with TMB substrate in the dark for 15 minutes, and then added ELISA stop solution (2N H$_2$SO$_4$). The value of OD 450 nm was measured by spectrophotometer. Referring to FIG. 4A-4B, the immunizations with stem-deglycosylated proteins elicited slightly but not significantly higher IgG titers compared to WT H5 and H1 proteins (H5 WT and H1 WT) homologous immunization. Further investigated the cross-reactive total IgG titers, after "H5 N10,11,23A" and "H5 HA N484A" immunization, cross-reactive IgG titers could be induced significantly higher than H5 WT group (FIG. 4C).

Figure 5:
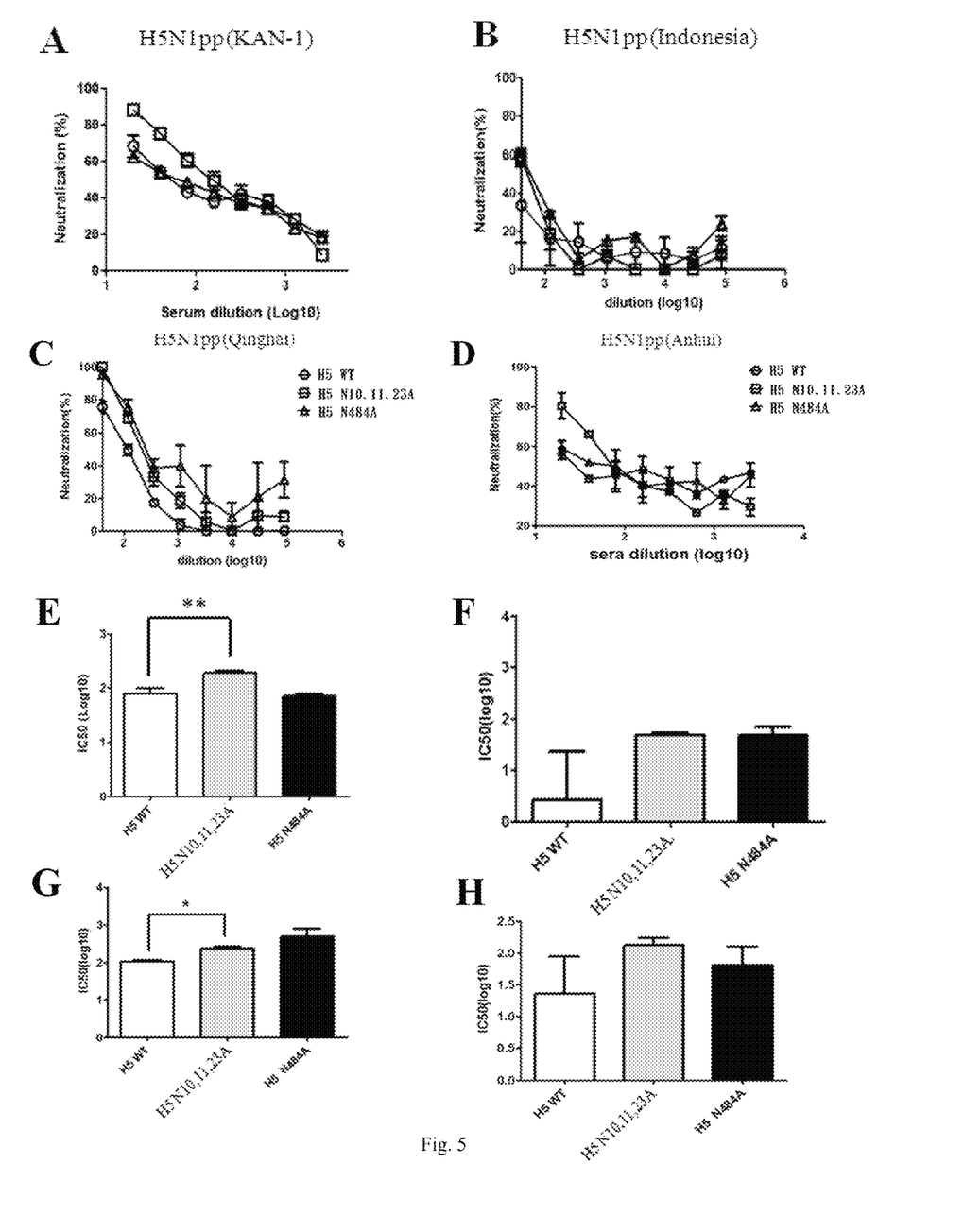
FIG. 5A-5H illustrate the neutralization curves and IC50 value against the different clades of H5N1pp virus by serum in mice immunized with stem-deglycosylated H5 HA.

Also, after H1 N503A immunization, the cross-reactive IgG could be elicited more than H1 WT.

c. Neutralizing Antibody Titers Against H5N1 in Serum Immunized with Deglycosylated H5 HAs 4×10$^6$ HEK 293A cells were prepared in 10 cm dish and co-transfected with pNL luc E$^-$ R$^-$, pcDNA 3.1 (+) encoding HA (A/Thailand/1(KAN-1)/2004), and pcDNA 3.1(+) encoding NA (A/Vietnam/1203/2004). After 48 hours transfection at 37° C., the pseudotyped viruses were collected and concentrated by 100 kDa centrifugal filters (MILLPORE). The pseudotyped virus titer was determined by luciferase activity. The serial diluted serum and 50 TCID$_{50}$ (the amount of a pathogenic agent that will produce pathological change in 50% of cell cultures inoculated) H5pp, was mixed with the same volume of 50 μl for 1 hour at 37° C. Then, the mixture was incubated with 1.5×10$^4$/well MDCK cells in 96-well white plates for another 48 hours at 37° C. Afterwards, the plates were washed by PBS, and followed by the same volume of lysis buffer and neolite for 5 minutes. Neutralizing antibody titers and log IC50 were quantified as reduced luciferase expression level following H5pp transduction in MDCK cells. Referring to FIG. 5A-5D, the neutralizing antibody responses against H5N1 (KAN-1, Qinghai, Anhui and Indonesia) showed neutralization curves in a dose-dependent manner, and H5 N10,11,23A and H5 N484A induced significantly higher neutralizing antibody titers (IC50=189.5; IC50=239.8) than H5 WT. H5 N10,11, 23A elicited a higher neutralizing antibodies against the homologous and heterosubtypic virus than H5 WT (FIGS. 5E and 5G).

d. Neutralizing Antibody Titers of pH1N1 in Serum Immunized with Deglycosylated H5 HAs Plagues reduction neutralization test (PRNT) was used to analyze the neutralizing antibody titer of the serum in the Example.

Figure 6:
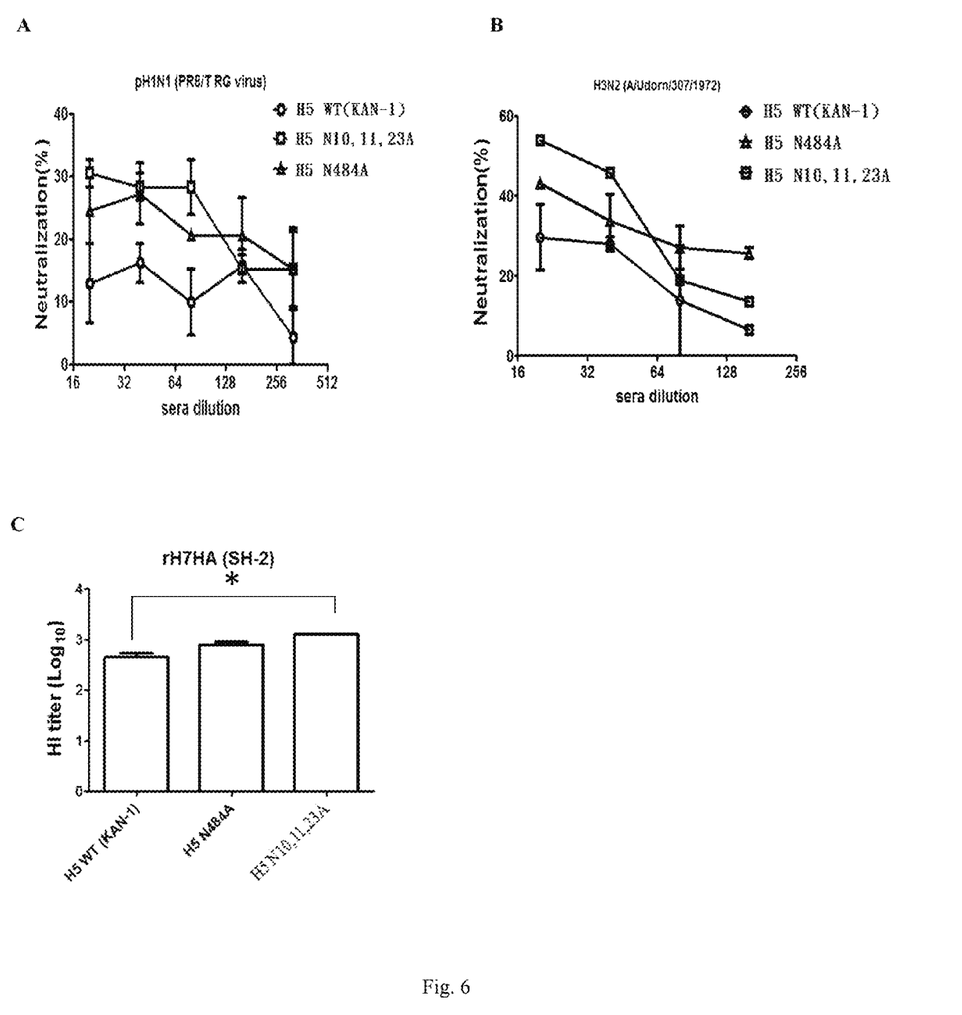
FIG. 6A-6B illustrate the neutralization ability against pH1N1 and H3N2 virus in serum from mice immunized with stem-deglycosylated H5 HA.
FIG. 6C illustrate that the serum of mice immunized with stem-deglycosylated H5 HA inhibits the hemagglutination of recombinant H7 HA protein.

MDCK cells were seeded in 6-well plate with 6×10$^5$ cells/well. Viruses were diluted with MEM-α containing 0.5 μg/ml TPCK-trypsin and mixed with pH1N1 virus (PR8x Texas 2009) at 37° C. for 1 hour to obtain the 50 PFU/50 μl of virus. The MDCK cells in 6-well plate were infected with the mixture of serum and virus at 37° C. for 1 hr. Afterward, the supernatant was removed with following PBS wash twice. 0.5% agarose of MEM-α was overlaid and incubated at 37° C. in 5% CO$_2$ for 2 days to determine the virus titer by counting the plague number using 2% of crystal violet. Referring to 6A and 6B, rH5HA protein could elicited neutralizing antibody against heterosubtypic pH1N1 and H3N2 (A/Udorn/307/1972) virus. For the stem-specific IgG titers elicited by stem-deglycosylated H5HAs, no significant differences were observed between H5 N484A and H5 N10,11,23A immunized groups.

e. Hemagglutination Inhibition (HAI) of Stem-Deglycosylated H5 HAs by H7HA

Figure 7:
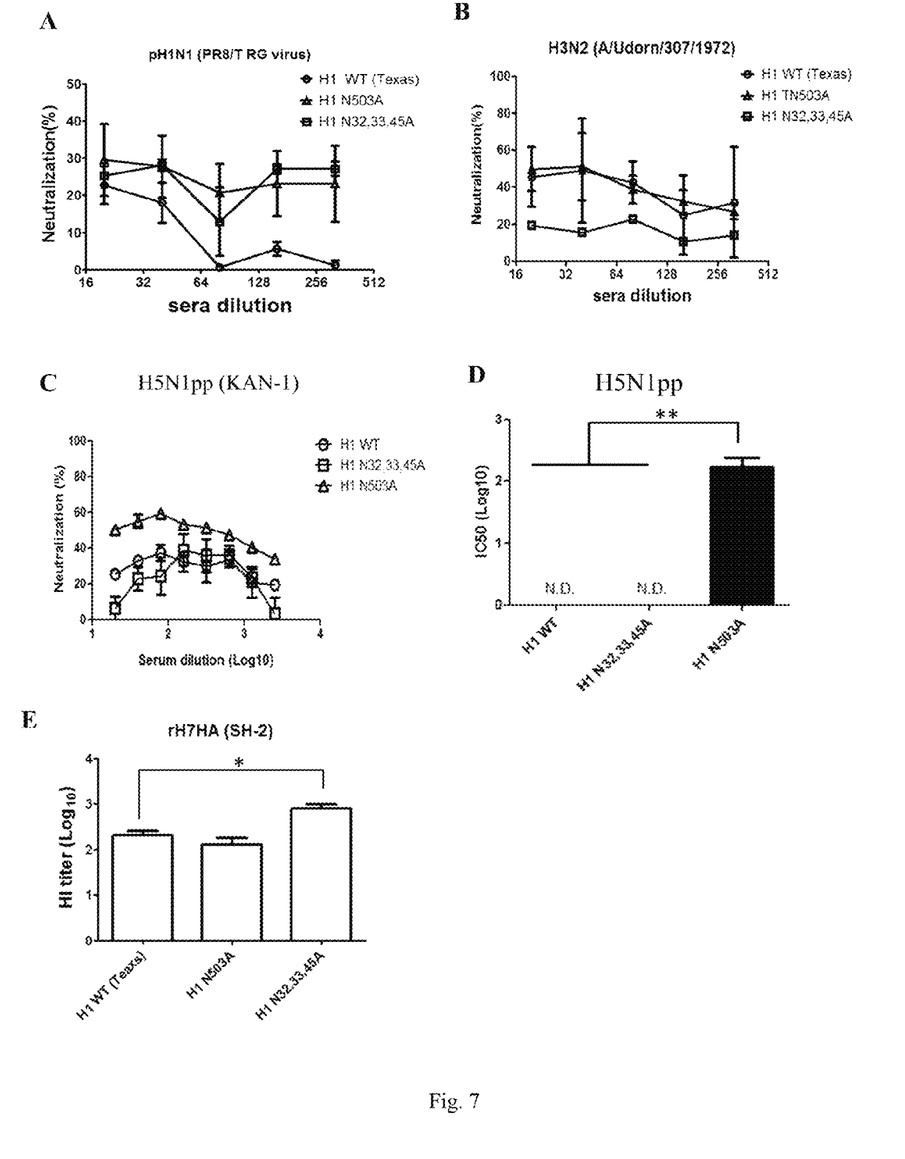
FIG. 7A-7D illustrate that the neutralization curve and IC50 value of pH1N1, H3N2, and H5N1pp virus by serum from mice immunized with stem-deglycosylated H1 HA.
FIG. 7E illustrates that the serum of mice immunized with stem-deglycosylated H1 HA inhibits the hemagglutination of recombinant H7 HA protein.

The serum and receptor-destroying enzyme (RDE) were mixed at a ratio of 1:3 and then reacted at 37° C. for 18-20 hours to remove the receptor interference. The RDE was inactivated by treatment of 56° C. for 30 minutes. Subsequently, the RDE treated serum was diluted, treated with 4 HA unit/25 μl recombinant H7HA (A/shanghai/2/2013 (H7N9)) protein at room temperature for 30 minutes, and then treated with 0.5% turkey red blood cells at room temperature for another 30 minutes to observe the hemagglutination of red blood cells. Referring to FIG. 6C, after administration of stem-deglycosylated H5HA protein vaccine, the protection capability met the requirement of WHO (HAI≥40). Compared to H5HA WT, stem-deglycosylated H5HA, particularly, H5 N10,11,23A had higher ability for inhibiting the red blood cells hemagglutination. The results indicate that H5HA of the invention provides broader protection against different subtypes and groups of influenza virus.

f. Neutralizing Antibody Titers Against pH1N1 in Serum Immunized with Stem-Deglycosylated H1 HAs The same procedure carried out in Example 3d was repeated except that the deglycosylated H5HAs protein was changed to deglycosylated H1HAs protein. Referring to FIG. 7A, the H1 N503A immunized groups showed the neutralization curves against homosubtypic pH1N1 virus in a dose-dependent manner. Besides, H1 N503A immunized group had higher neutralizing antibodies than H1 N32,33, 45A immunized group (FIG. 7A).

g. Neutralizing Antibody Titers Against H5N1 in Serum Immunized with H1 HAs

The same procedure carried out in Example 3c was repeated except that the deglycosylated H5 HAs protein was changed to deglycosylated H1 HAs protein. Referring to FIG. 7C, the H1 N32,33,45A and H1 N503A immunized groups showed the neutralization curves against heterosubtypic H5N1pp in a dose-dependent manner. Referring to FIG. 7D, the H1 503A immunized group had higher IC50 (431.3) than H1 N32,33,45A immunized group (2.758).

h. Neutralizing Antibody Titers Against H3N2 Virus in Serum Immunized with Stem-Deglycosylated H1 HAs The same procedure carried out in Example 3f was repeated except that the pH1N1 virus (PR8x Texas 2009) was changed to H3N2 (Udorn) virus. Referring to FIG. 7B, the H1 N503A immunized groups showed the neutralization curves against heterosubtypic H3N2 virus in a dose-dependent manner. For the production of neutralizing antibodies against heterosubtypic H3N2, no significant differences were observed between immunized groups (FIG. 7B).

i. Hemagglutination Inhibition (HAI) of Stem-Deglycoylated H1 HAs by H7HA

The same procedure carried out in Example 3e was repeated except that the deglycosylated H5HAs protein was changed to deglycosylated H1HAs protein. Referring to FIG. 7E, H1 N32,33,45A had a higher HI titer. The results indicate the H1 N32,33,45A provided broader cross-protection against heterologous and different strains of viruses.

According to the results of Examples 3c-3i, the neutralizing antibodies against homologous and different clades of H5N1 virus are elicited by the stem-deglycosylated H5 N10,11,23A, which also has high ability for inhibiting the hemagglutination of H7HA. Additionally, all of the stem-deglycosylated H1 N503A and H1 N32,33,45A elicit the production of neutralizing antibodies against homologous pH1N1 virus, wherein a higher titer of neutralizing antibodies against virus is induced by H1 N503A, and H1 N32,33, 45A provides higher HI titer of heterologous H7HA recombinant protein.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A multivalent influenza virus vaccine, comprising:
    a deglycosylated hemagglutinin which has an HA1 module and an HA2 module, and the HA1 and HA2 contain a stem region and a head region, and
    a pharmaceutically acceptable adjuvant or carrier,
    wherein glycosylation sites of the HA1 and HA2 on the stem region are removed and the deglycosylation site amino acid residues are Asparagine,
    wherein deglycosylation of glycosylation sites of the HA1 and HA2 results from substitution of Asparagine with Alanine,
    wherein the hemagglutinin is a hemagglutinin of avian H5N1 influenza virus,
    wherein the stem region of the hemagglutinin of the avian H5N1 influenza virus comprises amino acids at positions 343 to 527 of the HA2 module,
    wherein the deglycosylation site comprises an amino acid at position 484 of the HA2 module on the stem region of the hemagglutinin of the avian H5N1 influenza virus.

2. The multivalent influenza virus vaccine as claimed in claim 1, wherein the stem region of the hemagglutinin of the avian influenza H5N1 virus comprises amino acids at positions 1 to 57 of the HA1 module.

3. The multivalent influenza virus vaccine as claimed in claim 1, wherein the deglycosylation site comprises amino acids at positions 10, 11, and 23 of the HA1 module on the stem region of the hemagglutinin of the avian H5N1 influenza virus.

* * * * *